United States Patent
Hoogenakker et al.

(10) Patent No.: US 7,484,531 B2
(45) Date of Patent: Feb. 3, 2009

(54) MIDDLE EAR PRESSURE EQUALIZING DEVICE WITH IMPROVED PRESSURE CONTROL

(75) Inventors: Jon E. Hoogenakker, Inver Grove Heights, MN (US); James L. Lindenberg, Wyoming, MN (US)

(73) Assignee: Micromedics, Inc., St. Paul, MN (US)

( * ) Notice: Subject to any disclaimer, the term of this patent is extended or adjusted under 35 U.S.C. 154(b) by 552 days.

(21) Appl. No.: 11/146,791

(22) Filed: Jun. 7, 2005

(65) Prior Publication Data

US 2006/0272650 A1   Dec. 7, 2006

(51) Int. Cl.
*A61H 23/00* (2006.01)
*F16K 11/08* (2006.01)
(52) U.S. Cl. .................................. 137/879; 604/26
(58) Field of Classification Search ............ 137/118.06, 137/877, 879; 128/207.18; 604/26
See application file for complete search history.

(56) References Cited

U.S. PATENT DOCUMENTS

| | | | |
|---|---|---|---|
| 841,146 A * | 1/1907 | Hasbrouck | 601/10 |
| 976,200 A * | 11/1910 | Meyer | 601/77 |
| 2,014,009 A * | 9/1935 | Vance | 601/76 |
| 3,207,179 A * | 9/1965 | Klagues | 137/879 |
| 4,184,510 A * | 1/1980 | Murry et al. | 137/565.23 |
| 4,325,386 A * | 4/1982 | Katz | 600/546 |
| 4,754,748 A * | 7/1988 | Antowski | 601/76 |
| 4,757,807 A * | 7/1988 | Densert et al. | 601/76 |
| 4,774,945 A * | 10/1988 | White et al. | 128/207.18 |
| 4,915,105 A * | 4/1990 | Lee | 128/205.27 |
| 5,085,249 A * | 2/1992 | Dragan et al. | 137/879 |
| 5,419,762 A | 5/1995 | Arick et al. | |
| 5,885,242 A | 3/1999 | Arick et al. | |
| 6,159,171 A * | 12/2000 | Densert et al. | 601/76 |
| 6,629,938 B1 * | 10/2003 | Engvall et al. | 601/76 |
| 6,958,043 B2 * | 10/2005 | Hissong | 600/560 |

* cited by examiner

*Primary Examiner*—John Fox
(74) *Attorney, Agent, or Firm*—Westman, Champlin & Kelly, P.A.

(57) ABSTRACT

An apparatus for equalizing pressure in a middle ear includes a hand-held air source for providing a continuous flow of air at a predetermined rate and a tapered sealing nostril plug adapted to be sealed against a nostril. The tapered nostril plug has a channel there through for delivering the continuous flow of air. The channel of the tapered plug is adapted to be placed in communication with the air source through an adjustable valve assembly for selecting a pressure limit for the air in the channel of the nostril plug.

14 Claims, 2 Drawing Sheets

MIDDLE EAR PRESSURE EQUALIZING DEVICE WITH IMPROVED PRESSURE CONTROL

BACKGROUND OF THE INVENTION

I. Field of the Invention

This invention relates generally to a portable, hand-held apparatus for equalizing pressure in the middle ear, and more particularly to a device of the type described that provides improved control over the air pressure applied by the device to a patient's Eustachian tubes during a treatment procedure.

II. Discussion of the Prior Art

In U.S. Pat. Nos. 5,419,762 and 5,885,242 to Arick, et al. (the contents of which are hereby incorporated by reference), there is described an apparatus for facilitating the Politzer maneuver for equalizing the pressure in the middle ear in patients suffering from Eustachian Tube Dysfunction (ETD) or Aerotitis Media. That apparatus comprises an electric-powered air source contained in a hand-held housing for providing a continuous flow of air to an exit port of the device. More particularly, a battery-powered DC motor, when energized, drives a small pump or compressor whose outlet is connected by a short length of plastic tubing contained in the housing to the device's exit port in a nozzle projecting from the housing and that is adapted to seal against one of the patient's nostrils. With the continuous flow of air into one nostril and with the other nostril pinched closed, the patient is asked to swallow. Swallowing closes the esophagus and directs air pressure to the Eustachian tube, opening it to allow any fluid to flow from the middle ear and/or to restore pressure balance to the middle ear.

The Arick, et al. '242 patent suggests that the applied pressure generated by the pump be limited to a lower pressure of about 1.5 psi for infants and small children and a higher pressure of about 3 psi for adults. For this purpose, a speed control circuit is coupled between the battery and the motor terminals. It has been found, however, that attempting to accurately regulate the pressure of the output air by controlling motor pump speed is less than satisfactory. Those skilled in the art recognize that the motor speed, and thus the pump's air flow rate is dependent on battery voltage and that battery voltage varies with the depletion state of the battery's charge as well as with temperature. One can understand, therefore, that the desired airflow rate, measured in liters-per-minute and in air pressure measured in pounds-per-square-inch that can be developed in a given time using the selector switch 20a in FIG. 7 of the '242 patent, may be difficult to maintain.

It is accordingly a principal object of the present invention to provide an improved apparatus for affecting the Politzer maneuver.

Another object of the invention is to provide a hand-held, battery-operated device containing a motor-driven pump for producing a continuous flow of air at the device outlet nozzle at a plurality of selectable pressure values that are independent of battery state over the expected life of the battery.

SUMMARY OF THE INVENTION

In its broadest sense, the present invention comprises an apparatus for equalizing pressure in the middle ear of a patient where the apparatus incorporates within a hand-held housing an electric-powered air source for providing a predetermined continuous flow of air to an exit port of the device and that has an adjustable valve assembly operatively coupled between the electrically-powered air source and the exit port for selecting a pressure limit for the air at the exit port.

Without limitation, the adjustable valve assembly may comprise a valve housing having an inlet port in fluid communication with the electrically-powered air source, an outlet port in fluid communication with the device's exit port, an exhaust port leading to the ambient and a valve seat located between the exhaust port and the inlet port. A spring biased ball cooperates with the valve seat to block airflow through the exhaust port so long as the air pressure at the exit port remains below a predetermined level. Means are then provided for varying the spring-biasing force on the ball to adjust the pressure at which the ball unseats.

Alternatively, the adjustable valve assembly may comprise a molded plastic manifold having an inlet port in fluid communication with the electrically-powered air source, an outlet port in fluid communication with the exit port and an exhaust port leading to the ambient where the manifold incorporates a rotatable turret carrying a plurality of check valves, where each of the check valves is adapted to open at different predetermined pressures. Rotation of the turret selectively places a selected one of the plurality of check valves in fluid circuit between the exhaust port and the inlet port.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
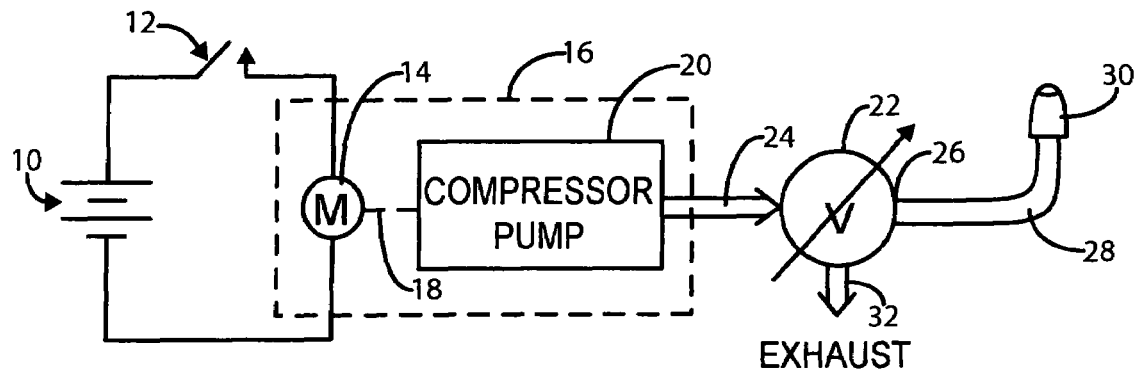
FIG. 1 is a schematic diagram showing the arrangement of the components used in the present invention.

Referring to the schematic diagram of FIG. 1, the improved apparatus for equalizing pressure in a patient's middle ear is seen to comprise a battery 10 that is connected through a single pole, single throw switch 12 to a small DC motor 14 of an electrically-powered air source, shown enclosed by the broken line box 16. The motor shaft 18 drives a compressor pump 20 for continuously producing air, under pressure, to the input of an adjustable valve assembly 22 by way of a tubing connection 24. The valve 22 has an outlet port 26 connected by tubing 28 to a nose piece 30. The adjustable valve 22 also has an exhaust port 32 leading to the ambient.

The valve 22 remains closed so long as the inlet air pressure from the compressor 20 is below a preset value. The valve remains closed, blocking the exhaust port while allowing air flow from the inlet 24 through the outlet 26 leading to the nose piece 30. However, when the pressure at the inlet port of the valve 22 reaches the preset valve, the valve opens, preventing any further increase in the pressure of the air reaching the nose piece 30.

Figure 2:
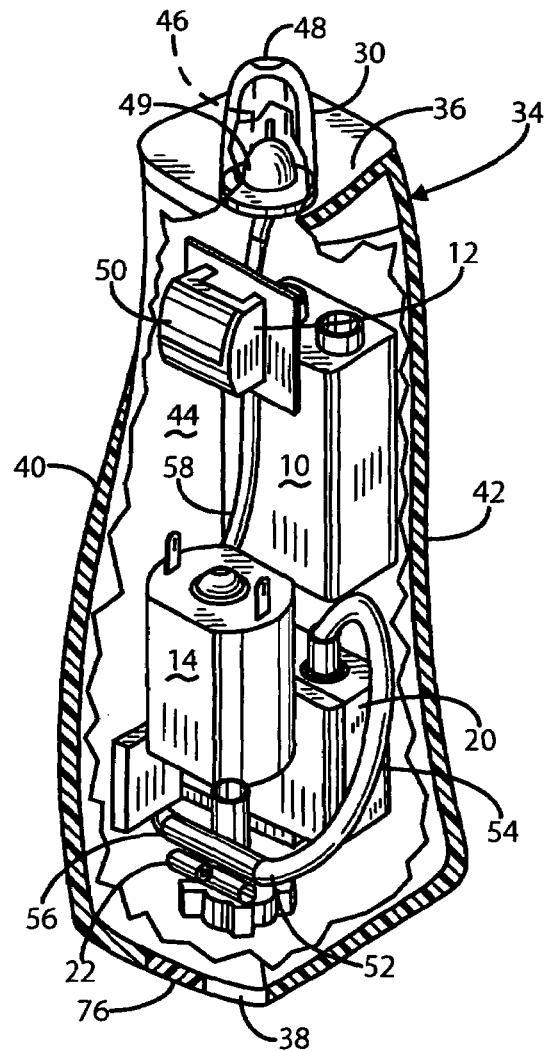
FIG. 2 is an isometric view of the housing comprising the hand-held device.

FIG. 2 is a cross-sectional view showing how the components of FIG. 1 may be placed within a hand-held housing. The housing itself is identified by numeral 34 and is preferably formed from a suitable plastic and it includes a top 36, a base 38 and four mutually perpendicular sidewalls, only three of which are seen in FIG. 2 including a front wall 40, a rear wall 42 and a left side wall 44. The conically-shaped nozzle 30 projects upwardly from the top surface 36. It may be permanently affixed to the top surface 36 or, preferably is removable and replaceable. The nozzle 30 includes a central 46 leading to an exit port 48 proximate its apex. It has also proved expedient to incorporate a duck-bill valve 49 in the nozzle which opens with air flow from the valve 22 but that serves to block expiratory flow carrying mucous back through the nozzle.

The electrical on/off switch 12 is shown as being located within the housing 34 but with an actuating member 50 projecting through the front wall 40 of the housing so as to be assessable to the user.

The power source (battery) 10 is suitably supported within the housing and provision is made so that the housing can be opened to gain access to the battery 10 for replacement purposes.

Also contained within the housing 34 is the motor-driven compressor 16 that includes a miniature DC motor 14 connected in driving relation to a compressor pump 20. The motor 14 and pump 20 is preferably an A-Series, Iron-Core Air Pump available from Sensidyne, Inc. capable of delivering from about 0.1 to about 3.5 l/min at a pressure of up to 10 psig. The combination motor and pump occupies only 3.4 cubic in. and weighs approximately 2.9 oz. The pump 20, itself, is a diaphragm pump. While the Sensidyne Micro Air Pump is well suited to the present application, other commercially available DC motor driven pumps are commercially available from other suppliers and limitation to the Sensidyne A-Series motor-driven pump is not intended.

The adjustable valve assembly 22 is supported by the base 38 of the housing and it has a valve inlet 52 connected by plastic tubing 54 to the outlet of the pump 20. The valve outlet 56 is connected by flexible plastic tubing 58 to the bore 46 of the nose piece 30.

For clarity in the drawings, the electrical wires connecting the battery 10, the switch 12 and the motor 14 in series are not shown.

Figure 3:
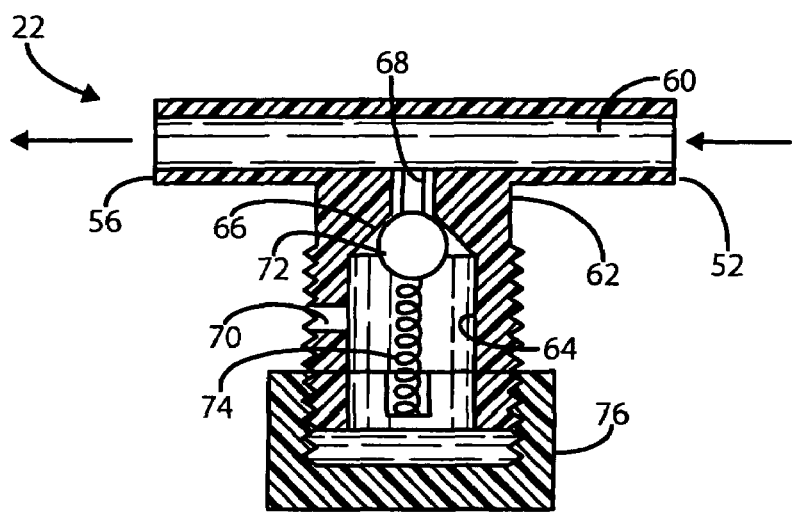
FIG. 3 is an exploded view of an adjustable valve assembly usable in the combination of FIG. 1.

Referring next to FIG. 3, there is shown the make-up of one type of pressure adjustable valve that can serve as the valve 22. It includes a tubular air flow passage 60 leading from the valve inlet 52 to its outlet 56. The tubular flow passage 60 is integrally molded with a valve housing 62 that includes a central bore 64 leading to a frusto-conically shaped valve seat 66 located between the bore 64 and a counterbore 68 leading to the passage 60. A transversely extending bore 70 is formed through the wall of the valve housing 62.

Contained within the bore 64 is a ball valve member 72 that is urged against the seat 66 by a spring 74. An adjusting nut 76 is internally threaded so as to mate with the external threads on the valve housing 62. By rotating adjusting nut 76 to the right, the biasing force of the spring 74 on the ball 72 is increased, thus requiring a higher air pressure in the passage 60 to unseat the ball. Turning the adjustment nut 76 to the left when viewed as in FIG. 3 decreases the spring biasing force on the ball 72, thus lessening the amount of air pressure in the passageway 60 needed to unseat the ball and allow air flow out through the bore 70.

The adjustable valve assembly 22 is mounted in the housing 34 of FIG. 2 such that the adjustment nut 76 is exposed and assessable to allow its rotation.

Assuming that the pump 20 is capable of delivering air at a pressure of 10 psig and the valve is adjusted such that a pressure of 3 psig will unseat the ball 72, the excess pressure will then be relieved through the port 70 in the valve housing 62. If desired, a suitable detent can be placed between the adjusting nut 76 and the valve housing 62 to establish plural predetermined pressure settings for the adjustable valve assembly 22. Without limitation, the detent may permit selection of, say, 1.5 psi, 2.5 psi, 5 psi and 10 psi. It has been found than the incorporation of the adjustable valve 22 in the hand-held device yields a more precise control of the air pressure at the exit port 48 that is achievable using a speed control circuit for regulating the speed of the motor 14 driving the pump 20.

Figure 4:
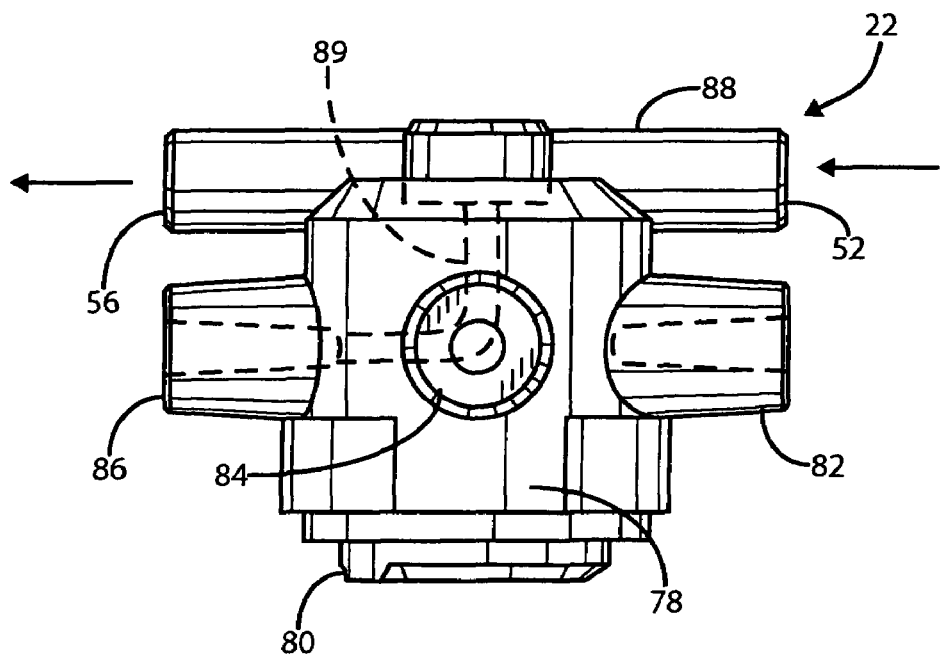
FIG. 4 is an alternative design for an adjustable valve assembly usable in implementing the present invention.

FIG. 4 illustrates an alternative construction of an adjustable valve assembly that can be used as a valve 22 in the hand-held device used for equalizing pressure in the middle ear of a patient. It is seen to comprise a molded plastic valve body 78 having a cylindrical cavity for receiving a rotatable turret 80 therein. Integrally molded with the housing member 78 are a plurality of exhaust ports 82, 84 and 86. Disposed in each of the exhaust ports is a check valve, each designed to open at a different predetermined pressure. For example, the check valve (not shown) inserted within the exhaust port 82 may be designed to open at 1.5 psi, the check valve contained within the exhaust port 84 to open at 2½ psi and the check valve within the exhaust port 86 designed to open at 5 psi.

Also integrally molded with the housing 78 is a flow passage comprising a tube 88. The outlet of the pump 20 connects by tubing 54 to the valve inlet 52. The valve outlet 56 is coupled by tubing 58 to the bore 46 in the nozzle 30. The turret 80 includes an L-shaped passageway 89 with one leg of the L in fluid communication with the interior of the tube 88 and the other leg of the L exiting the turret 80 at a location that sequentially aligns with the exhaust ports 82, 84 and 86 as the turret 80 is rotated.

In operation, with the turret set so that the L-shaped passage has its one leg aligned with the exhaust port 82, it may take a pressure of 1.5 psi to open the check valve in the exhaust port 82. In a similar manner, when the turret 80 is rotated so that the one leg of the L-shaped bore aligns with the exhaust port 84, the check valve contained therein will only open when the pressure in tube 88 equals or exceeds 2.5 psi. Assuming that the check valve associated with the exhaust port 86 requires 5 psi to actuate it, a user may select 5 psi as the desired pressure for application through the nose piece 30 by rotating the turret 80 until the one leg of the L-shaped bore formed in the turret aligns with the exhaust port 86. Again, the adjustable valve assembly of FIG. 4 is disposed in the hand held housing 34 so that the rotatable turret 80 is accessible through the base 38 of the housing 34.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. In an apparatus for equalizing pressure in the middle ear having an electric powered air source for providing a predetermined continuous flow of air to an exit port of a hand-held device, the improvement comprising:
   (a) an adjustable valve assembly operatively coupled between the electrically powered air source and the exit port for selecting a pressure limit of the air at said exit port, wherein the adjustable valve assembly comprises:
      (i) a manifold having an inlet port in fluid communication with the air source, an outlet port in fluid communication with the exit port and a plurality of exhaust ports leading to the ambient;

(ii) a corresponding plurality of check valves, each of the check valves adapted to open at different predetermined pressures operatively disposed in said plurality of exhaust ports; and (iii) a rotatable member contained in the manifold for selectively directing fluid from the inlet port to an individual one of the exhaust ports, the rotatable member having a fluid flow passage.

2. The apparatus of claim 1 wherein the pressure limit is in a range from about 1 psi to about 10 psi.

3. The apparatus as in claim 2 wherein the continuous flow is in a range from about 0.1 liters/minute to about 3.5 liters/minute.

4. The apparatus as in claim 1 wherein the adjustable valve assembly comprises:

(a) a valve housing having an inlet port in fluid communication with the air source, an outlet port in fluid communication with the exit port, an exhaust port leading to the ambient and a valve seat located between the exhaust port and the inlet port;

(b) a spring biased ball valve adapted to engage the seat to block air flow through the exhaust port as long as the air pressure at the exit port remains below a predetermined level; and (c) means for varying the spring biasing force on said ball.

5. The apparatus of claim 4 wherein the means for varying the spring biasing force on the ball includes an internally threaded cap for engaging external threads on the housing, said cap cooperating with a spring that engages the ball whereby rotation of the cap varies spring pressure on the ball.

6. The apparatus as in claim 1 wherein a first of the plurality check valves opens at about 1½ psi, a second of the plurality of check vales opens at about 2½ psi and a third of said plurality of check valves opens at about 10 psi.

7. The apparatus as in either claim 1 or claim 4 and further including a one-way valve disposed proximate the exit port for blocking body fluids from entering an interior of the hand-held device.

8. The apparatus as in claim 7 wherein the one-way valve is a duck bill valve.

9. In an apparatus for equalizing pressure in the middle ear having an electric powered air source for providing a predetermined continuous flow of air to an exit port of a hand-held device, the improvement comprising:

(a) an adjustable valve assembly operatively coupled between the electrically powered air source and the exit port for selecting a pressure limit of the air at said exit port; and (b) a one-way valve disposed proximate the exit port for blocking body fluids from entering an interior of the hand-held device.

10. The apparatus of claim 9 wherein the pressure limit is in a range from about 1 psi to about 10 psi.

11. The apparatus as in claim 10 wherein the continuous flow is in a range from about 0.1 liters/minute to about 3.5 liters/minute.

12. The apparatus as in claim 9 wherein the adjustable valve assembly comprises:

(a) a valve housing having an inlet port in fluid communication with the air source, an outlet port in fluid communication with the exit port, an exhaust port leading to the ambient and a valve seat located between the exhaust port and the inlet port; (b) a spring biased ball valve adapted to engage the seat to block air flow through the exhaust port as long as the air pressure at the exit port remains below a predetermined level; and (c) means for varying the spring biasing force on said ball.

13. The apparatus of claim 12 wherein the means for varying the spring biasing force on the ball includes an internally threaded cap for engaging external threads on the housing, said cap cooperating with a spring that engages the ball whereby rotation of the cap varies spring pressure on the ball.

14. The apparatus as in claim 12 wherein the one-way valve is a duck bill valve.

\* \* \* \* \*

UNITED STATES PATENT AND TRADEMARK OFFICE
CERTIFICATE OF CORRECTION

PATENT NO.         : 7,484,531 B2  Page 1 of 1
APPLICATION NO. : 11/146791
DATED              : February 3, 2009
INVENTOR(S)       : Jon E. Hoogenakker It is certified that error appears in the above-identified patent and that said Letters Patent is hereby corrected as shown below:

<u>Column 5, Claim 6</u>

Line 32, change "$^{1}\!\!/_{2}$" to -- 1 ½ --

Line 33, change "$^{2}\!\!/_{2}$" to -- 2 ½ --

Signed and Sealed this

Twenty-eighth Day of April, 2009

JOHN DOLL
*Acting Director of the United States Patent and Trademark Office*